(12) United States Patent
Engell et al.

(10) Patent No.: US 11,565,257 B2
(45) Date of Patent: *Jan. 31, 2023

(54) STABILIZED RADIOLABELLING REACTION

(71) Applicant: GE Healthcare Limited, Buckinghamshire (GB)

(72) Inventors: Torgrim Engell, Oslo (NO); Alexander Jackson, Buckinghamshire (GB); Imtiaz Ahmed Khan, Buckinghamshire (GB); Alan Peter Clarke, Oslo (NO); Graeme McRobbie, Buckinghamshire (GB); Julian Grigg, Buckinghamshire (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/043,445

(22) PCT Filed: Mar. 29, 2019

(86) PCT No.: PCT/EP2019/058111
§ 371 (c)(1),
(2) Date: Sep. 29, 2020

(87) PCT Pub. No.: WO2019/185932
PCT Pub. Date: Oct. 3, 2019

(65) Prior Publication Data
US 2021/0017098 A1    Jan. 21, 2021

(30) Foreign Application Priority Data
Mar. 29, 2018    (GB) ..................................... 1805253

(51) Int. Cl.
| | | |
|---|---|---|
| A61K 51/00 | (2006.01) | |
| A61M 36/14 | (2006.01) | |
| B01L 3/00 | (2006.01) | |
| C07B 59/00 | (2006.01) | |
| C07D 237/16 | (2006.01) | |
| B01J 19/00 | (2006.01) | |

(52) U.S. Cl.
CPC ....... *B01L 3/502753* (2013.01); *B01J 19/004* (2013.01); *C07B 59/002* (2013.01); *C07D 237/16* (2013.01); *B01L 2200/0631* (2013.01); *C07B 2200/05* (2013.01)

(58) Field of Classification Search
CPC .. B01J 19/004; C07B 59/002; C07B 2200/05; C07D 237/16
USPC .......................................... 424/1.89
See application file for complete search history.

(56) References Cited

U.S. PATENT DOCUMENTS

| | | | | |
|---|---|---|---|---|
| 2013/0064769 | A1* | 3/2013 | Cesati | C07D 237/16 424/1.89 |
| 2013/0274436 | A1* | 10/2013 | Engell | C07K 7/64 530/317 |
| 2015/0175553 | A1 | 6/2015 | Wouters et al. | |

FOREIGN PATENT DOCUMENTS

| | | |
|---|---|---|
| CN | 103958049 A | 7/2014 |
| WO | 2005061415 A1 | 7/2005 |
| WO | 2007141529 A1 | 12/2007 |
| WO | 2011097649 A2 | 8/2011 |

OTHER PUBLICATIONS

Scott et al. Appl. Radiat. Isot. 67, 2009, 88-94.*
Great Britain Search Report received in Application No. GB1805253.0 dated Nov. 20, 2018, 4 pages.
International Search Report and Written Opinion received in Application No. PCT/EP2019/058111 dated Jul. 11, 2019, 10 pages.
Office Action received in Chinese Application No. 201980036255.4 dated Oct. 10, 2022, with translation, 17 pages.
Purohit et al., "Synthesis and Biological Evaluation of Pyridazinone Analogues as Potential Cardiac Positron Emission Tomography Tracers," J. Med. Chem. 2008, 51, 10, 2954-2970, Apr. 19, 2008, 7 pages.

* cited by examiner

*Primary Examiner* — Michael G. Hartley
*Assistant Examiner* — Sean R Donohue
(74) *Attorney, Agent, or Firm* — Jeff B. Vockrodt; Culhane Meadows, PLLC

(57) ABSTRACT

The present invention provides a method for the synthesis of an injectable composition comprising a [$^{18}$F]-labelled pyridaben derivative that is advantageous over prior methods. In particular, the method of the present invention comprises a method of radiosynthesis that permits a more facile purification using solid phase extraction (SPE).

16 Claims, 4 Drawing Sheets

STABILIZED RADIOLABELLING REACTION

CROSS REFERENCE TO RELATED APPLICATIONS

This application is a filing under 35 U.S.C. § 371 of international application number PCT/EP2019/058111, filed Mar. 29, 2019, which claims priority to application number GB 1805253.0 filed on Mar. 29, 2018, the entire disclosures of each of which are hereby incorporated by reference.

TECHNICAL FIELD OF THE INVENTION

The present invention relates to diagnostic imaging agents useful for positron emission tomography (PET) imaging as well as to improved means for producing such imaging agents. More specifically, the present invention is directed to method of purifying a crude [$^{18}$F]-labelled pyridaben derivative which in turn can then be formulated into a composition suitable for injection for myocardial perfusion imaging and methods and devices for preparing same. More specifically, the present invention is directed to the automated synthesis and purification of a [$^{18}$F]-labelled pyridaben derivative by means of solid phase extraction (SPE).

DESCRIPTION OF RELATED ART

[$^{18}$F]-labelled pyridaben derivatives are known that find use in determining the presence or absence of a cardiovascular disease or condition in a subject. Methods for the synthesis of these [$^{18}$F]-labelled pyridaben derivatives are described in WO2011097649 A2 and comprise nucleophilic [$^{18}$F]-fluorination of an imaging agent precursor to form an imaging agent. The synthesis of an injectable composition comprising the compound [$^{18}$F]-flurpiridaz ([$^{18}$F]-FPZ) is described wherein the method comprises nucleophilic [$^{18}$F]-fluorination of a tosylate precursor compound, dilution with water followed by high-performance liquid chromatography (HPLC) purification.

Finding a purification method for [$^{18}$F]-FPZ that avoids HPLC is highly desirable and would result in easier accessibility for commercial application.

However, in developing a method using solid phase extraction (SPE) as the sole means of purification, a large percentage of a late-eluting product was observed that elutes very close to the desired product that to date can only be removed using a purification method comprising HPLC. The present inventors observed up to 22% of this radioimpurity. This results in a reduction in process yield and low radiochemical purity (RCP) of the final product as the radioimpurity elutes after [$^{18}$F]FPZ and can be present in the SPE elution.

There is therefore a need for improved methods for the synthesis of [$^{18}$F]FPZ.

SUMMARY OF THE INVENTION

The present invention provides:
In one aspect the present invention provides a method comprising reacting a precursor compound with $^{18}$F-fluoride in the presence of (2,2,6,6-Tetramethylpiperidin-1-yl)oxyl (TEMPO) to obtain an $^{18}$F-labelled compound wherein:
said precursor compound is of Formula I:

$$\text{BTM-LINKER-LG} \tag{I}$$

wherein:
BTM is an analogue of pyridaben;
LINKER is an alkylene or an alkoxyalkylene; and,
LG is a sulfonate-containing leaving group; and,
said $^{18}$F-labelled compound is of Formula II:

$$\text{BTM-LINKER-}^{18}\text{F} \tag{II}$$

wherein BTM and LINKER are as defined for Formula I
in another aspect the present invention provides a cassette for carrying out the method of the invention comprising:
i) a vessel containing the precursor compound as defined in claim 1;
ii) a vessel containing water;
iii) one or more SPE cartridges;
iv) a vessel containing a solution comprising an organic solvent;
v) a vessel containing a solution comprising ethanol;
vi) a vessel containing a hydrolysing reagent;
vii) TEMPO contained in a vessel or contained in said vessel containing the precursor compound;
viii) a reaction vessel;
ix) means for eluting the vessel of (i) with a suitable source of $^{18}$F;
x) means to transfer the precursor compound and suitable source of $^{18}$F to the reaction vessel;
xi) means to transfer the crude reaction mixture as defined in claim 1 to said one or more SPE cartridges;
xii) means to selectively transfer said water, said solution comprising an organic solvent and said solution comprising ethanol to said one or more SPE cartridges; and,
xiii) means to transfer said purified compound of Formula II as defined in claim 1 to a product collection vial.

The present inventors identified that the radioimpurity is formed due to radiolysis of [$^{18}$F]FPZ during the radiolabelling reaction. A number of radiostabilisers were tested Addition of TEMPO to the precursor reduces the radiolysis substantially, e.g. from up to 22% to 1% at 100 GBq starting activity. Therefore, addition of TEMPO to the labelling reaction has been found to reduce the amount of the late eluting radiolysis product and as a consequence allows subsequent purification to be carried out in a more facile manner. More specifically the present invention also permits using solid phase extraction (SPE) alone for purification of [$^{18}$F]FPZ.

DETAILED DESCRIPTION OF THE PREFERRED EMBODIMENTS

Figure 1:
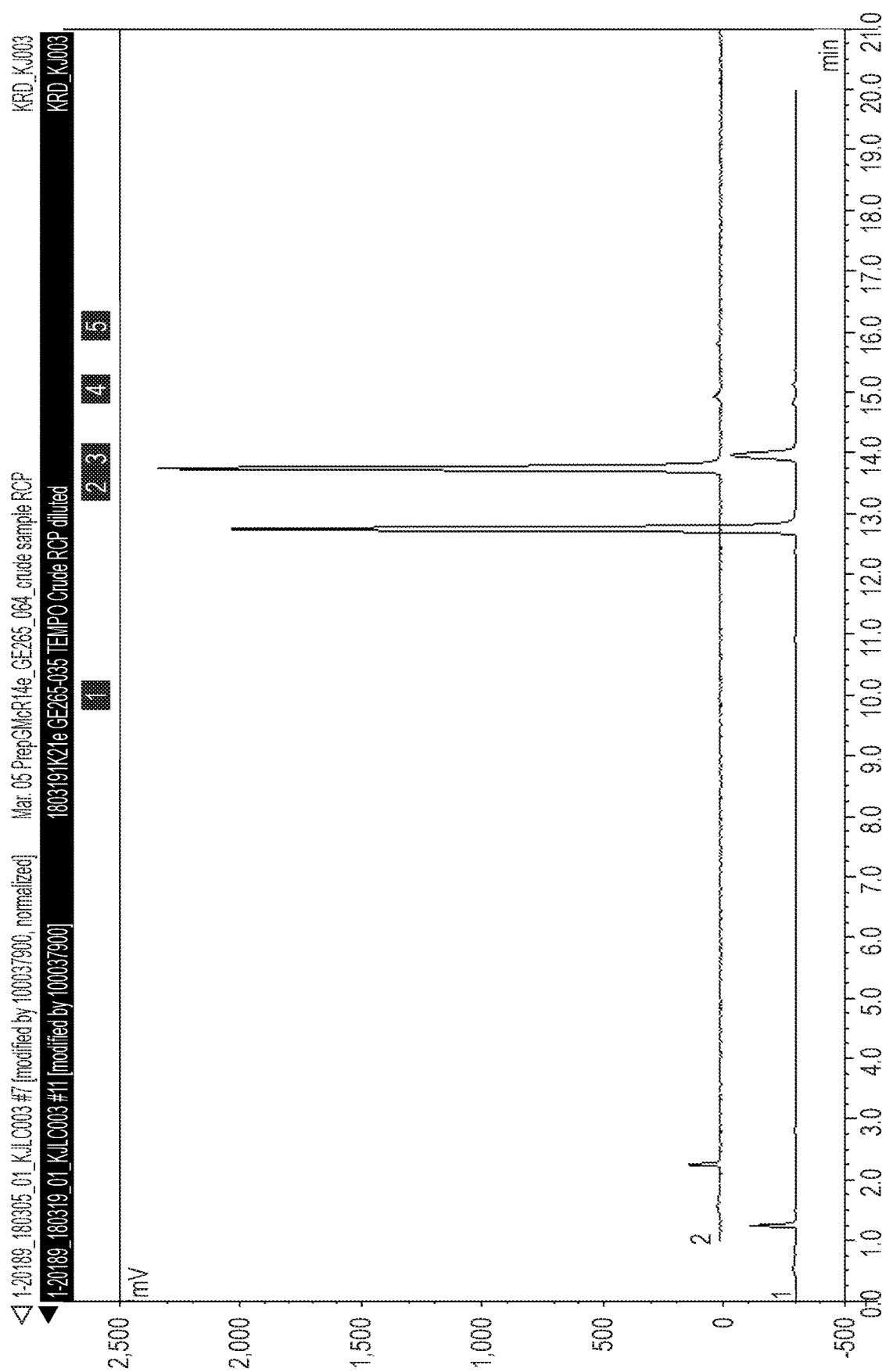
FIG. 1: Comparison of crude product with (top) and without (bottom) the addition of (2,2,6,6-Tetramethylpiperidin-1-yl)oxyl (TEMPO) to the labelling reaction.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

A "precursor compound" comprises a non-radioactive derivative of a radiolabelled compound, designed so that chemical reaction with a convenient chemical form of an in vivo-detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

The term "alkylene" refers to the bivalent group —$(CH_2)_n$— wherein n is preferably an integer from 1-6.

The term "alkoxyalkylene" means an alkylene as defined above comprising an ether linkage, where the term "ether linkage" refers to the group —C—O—C—.

The term "leaving group" refers to an atom or group of atoms that is displaced as a stable species during a substitution or displacement radiofluorination reaction. Suitable leaving groups for the present invention are sulfonate-containing leaving groups, where "sulfonate" means —$SO_3$.

The term "$^{18}F$-fluoride" refers to $^{18}F$-fluoride in a chemical form suitable for displacing LG of Formula I in a nucleophilic substitution reaction to result in a compound of Formula II. $^{18}F$-fluoride is normally obtained as an aqueous solution from the nuclear reaction $^{18}O(p,n)^{18}F$ and is made reactive by the addition of a cationic counterion and the subsequent removal of water. Suitable cationic counterions should possess sufficient solubility within the anhydrous reaction solvent to maintain the solubility of $^{18}F^-$. Suitable counterions include large but soft metal ions such as rubidium or caesium, potassium complexed with a cryptand such as Kryptofix™ 222 (K222), or tetraalkylammonium salts. A suitable tetraalkylammonium salt is tetrabutylammonium hydrogen carbonate. A detailed discussion of well-known $^{18}F$ labelling techniques can be found in Chapter 6 of the "Handbook of Radiopharmaceuticals" (2003; John Wiley and Sons: M. J. Welch and C. S. Redvanly, Eds.).

The method of the invention comprises inclusion of TEMPO.

Tetramethylpiperidin-1-yl)oxyl (TEMPO) is included in reacting step (a). In one embodiment TEMPO is present in a molar ratio to the precursor compound of between 0.01:1 and 5:1, preferably between 0.1:1 and 2:1, most preferably between 0.4:1 and 0.6:1, especially preferably around 0.5:1, e.g. 0.56:1.

In one embodiment of the method of the invention the starting radioactivity is between 100-1000 GBq.

In one embodiment of the method of the invention the starting radioactivity is between 100-750 GBq.

In one embodiment the method of the invention further comprising purification of said $^{18}F$-labelled compound by means of solid phase extraction (SPE).

In one embodiment said SPE is carried out using one or more SPE cartridges.

In one embodiment said one or more SPE cartridges are selected from a tC18 and a mixed mode SPE cartridge.

In one embodiment said one or more SPE cartridges are tC18 cartridges.

In one embodiment said one or more SPE cartridges are 2 tC18 cartridges.

The term "solid phase extraction (SPE)" refers to the well-known sample preparation process by which compounds in a solution are separated from each other based on their respective affinities for a solid (the "solid phase", or "stationary phase") through which the sample is passed and the solvent (the "mobile phase" or "liquid phase") in which they are dissolved. The result is that a compound of interest is either retained on the solid phase or in the mobile phase. The portion that passes through the solid phase is collected or discarded, depending on whether it contains the compound of interest. If the portion retained on the stationary phase includes the compound of interest, it can then be removed from the stationary phase for collection in an additional step, in which the stationary phase is rinsed with another solution known as an "eluent". For the present invention SPE is suitably carried out using at least one "SPE cartridge" (also often referred to as an "SPE column"), a variety of which are readily available commercially and typically as a column packed with solid phase. Most known solid phases are based on silica that has been bonded to a specific functional group, e.g. hydrocarbon chains of variable length (suitable for reverse-phase SPE), quaternary ammonium or amino groups (suitable for anion exchange), and sulfonic acid or carboxyl groups (suitable for cation exchange). SPE in the context of the present invention specifically excludes HPLC. In one embodiment two SPE cartridges fluidly connected in series are used in the present invention.

In certain embodiments, as will be known to a person skilled in the art, the mobile phase used with the SPE cartridge will depend on choice of SPE cartridge. For example, in one embodiment where the SPE is an Affinisep polymer, aqueous acetonitrile is a suitable organic solvent, for step (iii), a non-limiting example of which would be 40% acetonitrile and 60% water. The eluent for the same SPE cartridge can be aqueous ethanol, a non-limiting example of which is 60% ethanol and 40% water. In one embodiment when the SPE is C18, an ethanol-based organic solvent for step (iii) and for elution can be used. As a non-limiting example 30-40% ethanol in water for the solvent for step (iii) followed by ethanol elution, which can be less than 100% ethanol.

In one embodiment a hydrolysing reagent is added during the purification.

The term "hydrolysing reagent" refers to a reagent capable of hydrolysis wherein "hydrolysis" is a technical term well known to those of skill in the art, i.e. a reaction involving the breaking of a bond in a molecule using water, where the reaction mainly occurs between an ion and water molecules and often changes the pH of a solution. In chemistry, there are three main types of hydrolysis: salt hydrolysis, acid hydrolysis, and base hydrolysis.

In one embodiment, said hydrolysing reagent is acidic. Any suitable acid may be used. In one embodiment said acidic hydrolysing reagent comprises hydrochloric acid, sulphuric acid or phosphoric acid.

In one embodiment, said acidic hydrolysing reagent is HCl.

In one embodiment, said hydrolysing reagent is alkaline. Any suitable base may be used. In one embodiment, alkoxide, alkali metal hydroxides, or thiooxide bases can be used. In a further embodiment, the base is selected from the group consisting of sodium hydroxide, potassium hydroxide, sodium hydride, sodium thiomethoxide, sodium ethoxide, ammonia/ammonium hydroxide and sodium methoxide.

In one embodiment, said alkaline hydrolysing reagent is selected from NaOH, $NH_4OH$ and NaOMe. In another embodiment, said alkaline hydrolysing reagent is NaOH.

The BTM is an analogue of pyridaben. Methods to obtain suitable pyridaben analogues are known in the art.

In one embodiment certain compounds of Formula I can be obtained following or adapting the processes described in WO2011097649 A2, starting with etherification of the starting compounds comprising formulae:

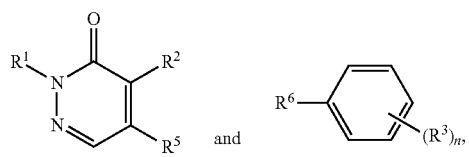

where n is 1,2,3,4, or 5; $R^1$ is alkyl, optionally substituted; $R^2$ is hydrogen or halide; $R^3$ can be the same or different and are alkyl, heteroalkyl, or a carbonyl-containing group, each optionally substituted, $R^5$ is hydroxyl or halide; and $R^6$ is alkyl, heteroalkyl, or a carbonyl-containing group, each optionally substituted, wherein, when $R^5$ is hydroxyl, at least one of $R^6$ and $R^3$ comprises a leaving group; or wherein $R^5$ is halide, at least one of $R^6$ or $R^3$ comprises a hydroxyl, to produce a compound comprising formula:

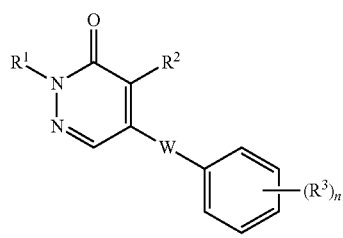

wherein W is alkyl or heteroalkyl, optionally substituted; $R^1$ is alkyl, optionally substituted; $R^2$ is hydrogen or halide; each $R^3$ can be the same or different and is alkyl optionally substituted with hydroxyl or heteroalkyl optionally substituted with hydroxyl; wherein at least one $R^3$ comprises hydroxyl; and n is 1,2,3,4, or 5; $R^1$ is alkyl, optionally substituted; $R^2$ is hydrogen or halide; $R^3$ can be the same or different and are alkyl, heteroalkyl, or a carbonyl-containing group, each optionally substituted. Then reacting this compound with a sulfonate-containing species such that at least one $R^3$ is converted to alkyl substituted with a sulfonate-containing group or heteroalkyl substituted with a sulfonate-containing group. This sulfonate-containing compound is a precursor compound of Formula I of the present invention. The sulfonate-containing precursor can then be reacted with $^{18}F$-fluoride to obtain compounds of Formula II of the present invention.

In one embodiment of the invention, said precursor compound is a compound of Formula Ia:

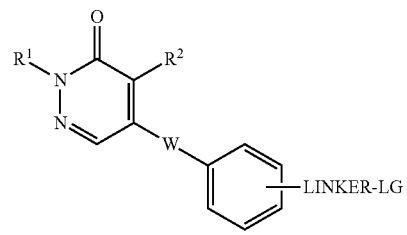

and said $^{18}F$-labelled compound is a compound of Formula IIa:

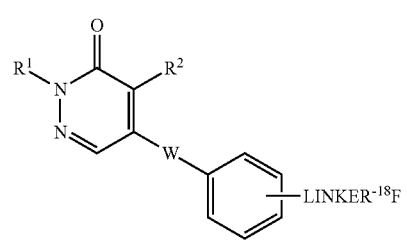

wherein:

$R^1$ is an optionally substituted $C_{1-6}$ alkyl;

$R^2$ is hydrogen or halo;

W is an optionally substituted alkylene or heteroalkylene;

LINKER and LG are as defined in claim 1.

In one embodiment $R^1$ of Formula Ia and Formula IIa is $C_{1-6}$ alkyl.

In one embodiment $R^1$ of Formula Ia and Formula IIa is methyl, ethyl, propyl, n-butyl, s-butyl, or t-butyl.

In one embodiment $R^2$ of Formula Ia and Formula IIa is halo.

In one embodiment $R^2$ of Formula Ia and Formula IIa is chloro.

In one embodiment W of Formula Ia and Formula IIa is heteroalkylene.

In one embodiment W of Formula Ia and Formula IIa alkoxyalkylene.

In one embodiment of the invention, said compound of Formula I is a compound of Formula Ib:

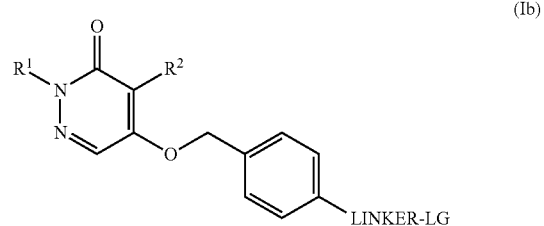

and said compound of Formula II is a compound of Formula IIb:

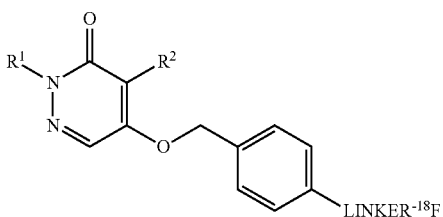

wherein $R^1$, $R^2$, LINKER and LG are as variously defined herein for Formula I and Formula II.

In one embodiment of the invention, said compound of Formula I is:

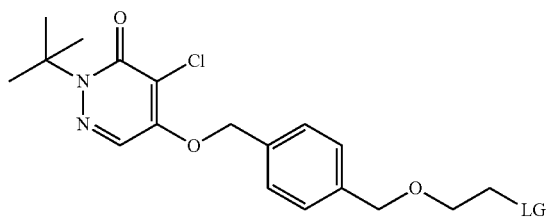

wherein LG is as variously defined herein;
and said compound of Formula II is:

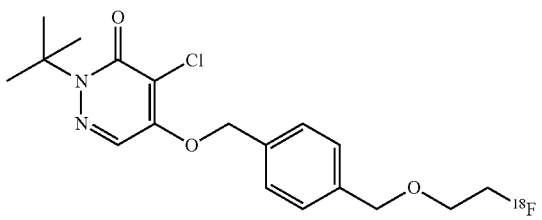

In one embodiment of the invention LG is selected from mesylate, tosylate, triflate, nosylate, or 1,2-cyclic sulfate.

In one embodiment of the invention LG is tosylate.

In one embodiment said precursor compound is dissolved in acetonitrile.

The method of the invention can be carried out using an automated synthesizer apparatus. By the term "automated synthesizer" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Such automated synthesizers are commercially available from a range of suppliers including: GE Healthcare; CTI Inc; Ion Beam Applications S.A. (Chemin du Cyclotron 3, B-1348 Louvain-La-Neuve, Belgium); Raytest (Germany) and Bioscan (USA).

An exemplary automated synthesizer carries out a radio-synthesis by means of a cassette. By the term "cassette" is meant a piece of apparatus designed to fit removably and interchangeably onto the automated synthesizer apparatus in such a way that mechanical movement of moving parts of the synthesizer controls the operation of the cassette from outside the cassette. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

A typical cassette has several positions for reagents and several suitable for attachment of syringe vials of reagents or chromatography cartridges (e.g. SPE). The cassette always comprises a reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture so are manufactured from materials of pharmaceutical grade and ideally also resistant to radiolysis.

In one embodiment the cassette is a disposable, single use cassette which comprises all the reagents, reaction vessels and apparatus necessary to carry out the method of the invention.

The cassette approach has the advantages of simplified set-up, reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs. the synthesis to be carried out; reagent traceability; single-use and hence no risk of cross-contamination, tamper and abuse resistance.

The present invention therefore also provides a cassette for carrying out the method of the invention comprising:
 i) a vessel containing the precursor compound as defined herein;
 ii) a vessel containing water;
 iii) one or more SPE cartridges;
 iv) a vessel containing a solution comprising an organic solvent;
 v) a vessel containing a solution comprising ethanol;
 vi) a vessel containing a hydrolysing reagent;
 vii) TEMPO contained in a vessel or contained in said vessel containing the precursor compound;
 viii) a reaction vessel;
 ix) means for eluting the vessel of (i) with a suitable source of $^{18}F$;
 x) means to transfer the precursor compound and suitable source of $^{18}F$ to the reaction vessel;
 xi) means to transfer the crude reaction mixture as defined herein to said one or more SPE cartridges;
 xii) means to selectively transfer said water, said solution comprising an organic solvent and said solution comprising ethanol to said one or more SPE cartridges; and,
 xiii) means to transfer said purified compound of Formula II as defined herein to a product collection vial.

In one embodiment TEMPO is present in a dedicated vessel on the cassette. In one embodiment TEMPO is present in the vessel containing the precursor compound, for example dissolved in acetonitrile.

The "organic solvent" suitably comprises a solvent known to those of skill in the art for SPE elution, for example tetrahydrofuran (THF), ethyl acetate and dichloromethane (DCM), dimethylformamide (DMF), acetonitrile (MeCN), dimethyl sulfoxide (DMSO), acetic acid, t-butanol, isopropanol, n-propanol, ethanol (EtOH) and methanol (MeOH). The organic solvent may be provided as an aqueous solution of said solvent.

In one embodiment the cassette further comprises a vial containing a hydrolysing reagent as defined herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes the radiosynthesis of crude [18F] Flurpiridaz.

Example 2 describes the radiosynthesis of crude [18F] Flurpiridaz with the addition of TEMPO.

Examples 3 and 4 describe the radiosynthesis of [18F] Flurpiridaz with SPE purification.

Example 5 describes the automated synthesis and purification of [$^{18}$F]Flurpiridaz.

Example 6 describes alternative ways for the radiosynthesis of [18F]Flurpiridaz with SPE purification.

LIST OF ABBREVIATIONS USED IN THE EXAMPLES

EtOH ethanol
HPLC high performance liquid chromatography
MeCN acetonitrile
PBS phosphate buffered saline
QMA quaternary methyl ammonium
RAC radioactive concentration
SPE solid phase extraction
TEMPO (2,2,6,6-Tetramethylpiperidin-1-yl)oxyl

EXAMPLES

Example 1: Radiosynthesis of Crude [$^{18}$F]Flurpiridaz.

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammonium hydrogen carbonate (22 mg) in water (100 µL) and acetonitrile (400 µL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg, synthesized according to known methods) in MeCN (1.7 mL) was added to the dried [$^{18}$F]-fluoride and the reaction mixture was heated at 120° C. for 10 minutes. The crude product was diluted with water (9.3 mL) and analysed by HPLC.

The % of [$^{18}$F]Flurpiridaz in the crude product was 81% with 13% of a late eluting radiolysis product (FIG. 1). In once instance of the radiosynthesis the inventors observed only 72% [$^{18}$F]Flurpiridaz.

Example 2: Radiosynthesis of Crude [$^{18}$F]Flurpiridaz with the Addition of TEMPO.

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammonium hydrogen carbonate (22 mg) in water (100 µL) and acetonitrile (400 µL). Nitrogen was used to drive the solution off the QMA cartridge to the reaction vessel. The [$^{18}$F]-fluoride was dried for 9 minutes at 120° C. under a steady stream of nitrogen and vacuum. A mixture of the precursor (10.2 mg) and TEMPO (1.7 mg) in MeCN (1.7 mL) was added to the dried [$^{18}$F]-fluoride and the reaction mixture was heated at 120 C for 10 minutes. The crude product was diluted with water (9.3 mL) and analysed by HPLC.

The % of [$^{18}$F]Flurpiridaz in the crude product was 92% with 1% of the late eluting radiolysis product. The addition of TEMPO to the labelling reaction reduces the amount of the late eluting radiolysis product (FIG. 1). The present inventors deduce from these results that even when carried out at high activity the addition of TEMPO to the radiolabelling reaction acts to reduce the late eluting radiolysis product.

Example 3: Radiosynthesis of [$^{18}$F] Flurpiridaz with EtOH-Based SPE Purification

Figure 2:
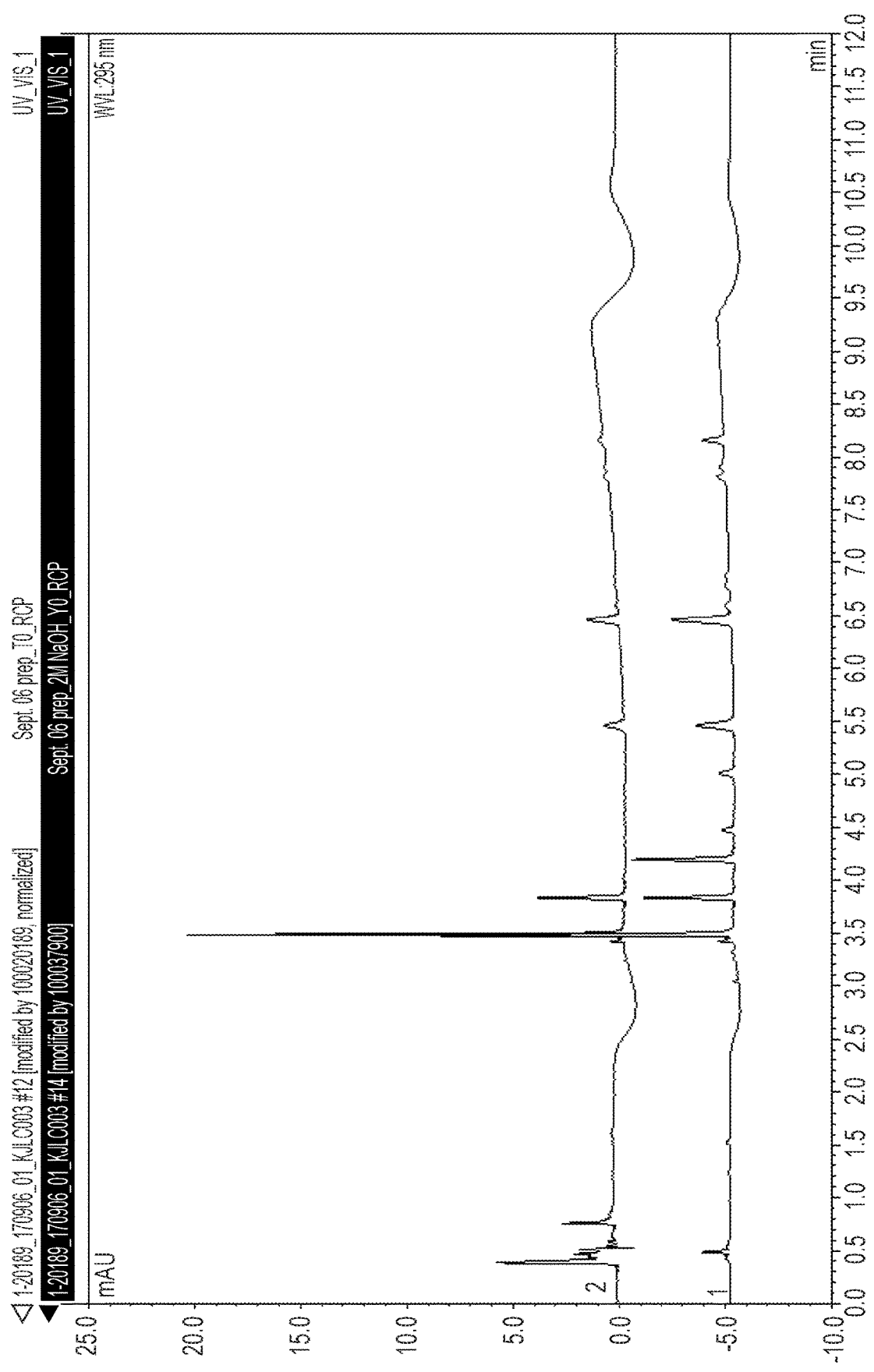
FIG. 2: Comparison of crude product with (top) and without (bottom) hydrolysis with NaOH post labelling reaction. The species in the 4-5 minute region are almost completely removed by the hydrolysis reaction.

[$^{18}$F]-fluoride (ca. 100 GBq) was produced using a GE Medical Systems PETtrace cyclotron with a silver target via the [$^{18}$O](p,n) [$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammonium hydrogen carbonate (22 mg) in water (100 µL) and acetonitrile (400 µL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg) in MeCN (1.7 mL) was added to the dried [$^{18}$F]-fluoride and the reaction mixture was heated at 120 C for 10 minutes. The crude product was diluted with 2 M NaOH (1.3 mL) and water (4 mL) and left to stand for 60 seconds (see FIG. 2 for comparison of with and without NaOH hydrolysis). The crude product was then loaded onto a tC18 SPE cartridge (Waters, product number WAT036800) and purified using the method described below.

The SPE cartridge was washed with water (30 mL) to wash away the acetonitrile, NaOH and hydrophilic chemical and radiochemical impurities. Then the SPE cartridge was washed with a 35% ethanol solution in water (25 mL) to remove the hydroxy impurity. After this, the first SPE cartridge was connected in series to a second SPE cartridge (Waters, product number WAT036800) and the two were washed with a 40% ethanolic water solution (14 mL) followed by a stream of nitrogen to transfer the [$^{18}$F] Flurpiridaz onto the second cartridge and trap the more lipophilic chemical and radiochemical impurities. The second SPE cartridge was then eluted with a 70% ethanolic solution (3 mL) to elute the [$^{18}$F]Flurpiridaz into the product vial. The 25 mL product vial was composed of water (23 mL), ethanol (2 mL) and ascorbic acid (50 mg/mL). See FIG. 3 for a chromatogram of the SPE purified product with and without ascorbic acid present.

Figure 3:
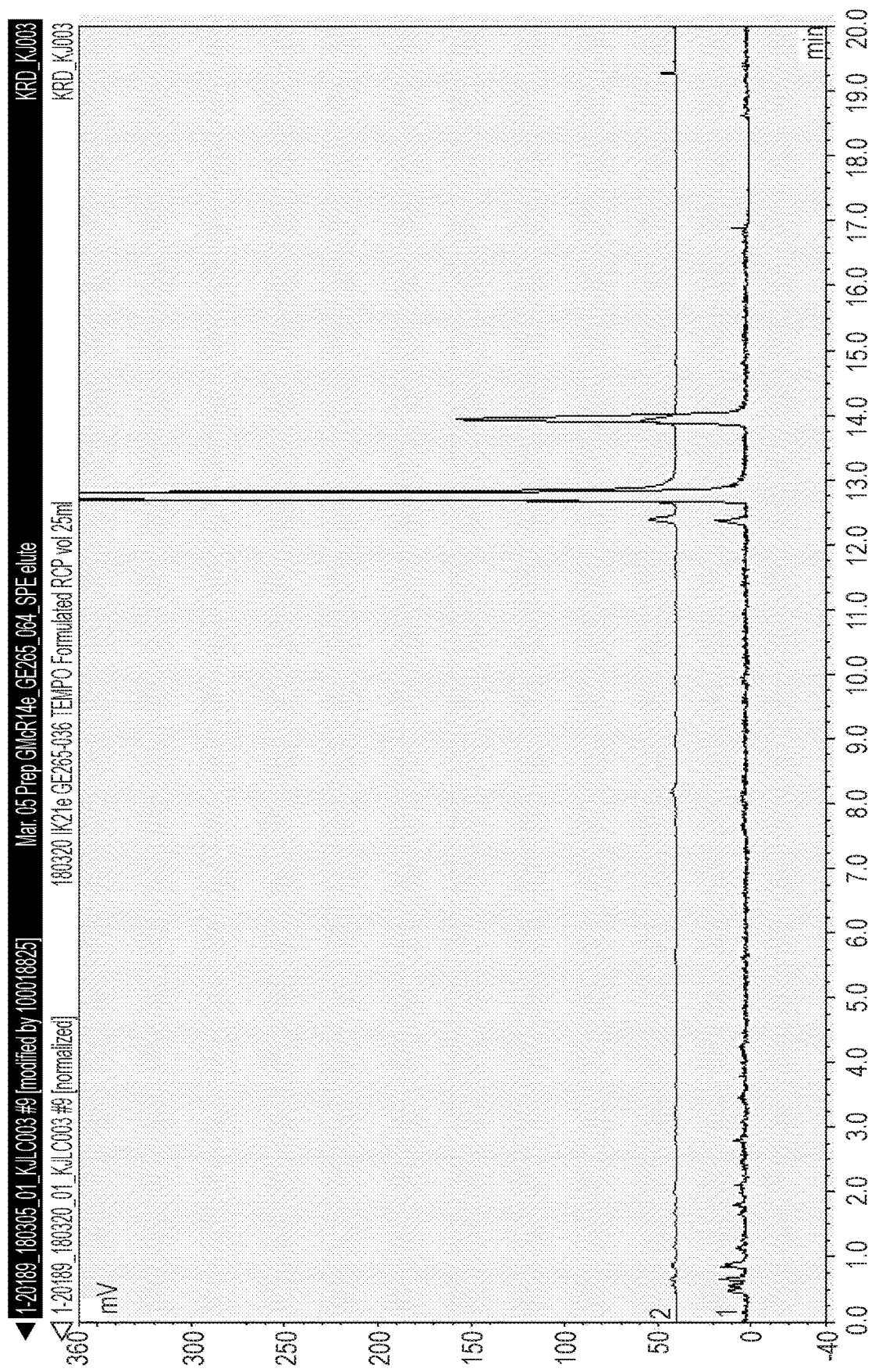
FIG. 3: Comparison of SPE purified product with (top) and without (bottom) ascorbic acid present in the product vial.

The non decay corrected yield was 43%, resulting in a product with an RAC of 1,800 MBq/mL. The RCP of the final product was 97%. Two radiolysis products were observed (1°/0 and 2% respectively). When ascorbic acid is excluded from the product vial, the RCP is 85-88% (FIG. 3).

Example 4: Radiosynthesis of [$^{18}$F]Flurpiridaz with EtOH-Based SPE Purification

[$^{18}$F]-fluoride (ca. 100 GBq) was produced using a GE Medical Systems PETtrace cyclotron with a silver target via the [$^{18}$O](p,n)[$^{18}$F] nuclear reaction. Total target volumes of 3.2-4.8 mL were used. The radiofluoride was trapped on a Waters QMA cartridge (pre-conditioned with carbonate), and the fluoride was eluted with a solution of tetrabutylammnonium hydrogen carbonate (22 mg) in water (100 µL) and acetonitrile (400 µL). Nitrogen was used to drive the solution off the QMA cartridge to the reaction vessel. The [$^{18}$F]fluoride was dried for 9 minutes at 120° C. under a steady stream of nitrogen and vacuum. The precursor (10.2 mg) in MeCN (1.7 mL) was added to the dried [$^{18}$F]-fluoride and the reaction mixture was heated at 120 C for 10 minutes. The crude product was diluted with 2 M NaOH (1.3 mL) and water (4 mL) and left to stand for 60 seconds (see FIG. 2 for comparison of with and without NaOH hydrolysis). The crude product was then loaded onto a tC18 SPE cartridge (Waters, product number WAT036800) and purified using the method described below.

The SPE cartridge was washed with water (30 mL) to wash away the acetonitrile, NaOH and hydrophilic chemical and radiochemical impurities. Then the SPE cartridge was washed with a 40% acetonitrile solution in water (10 mL) to remove the hydroxy impurity. After this, the first SPE cartridge was connected in series to a second SPE cartridge (Waters, product number WAT036800) and the two were washed with 40% acetonitrile (25 mL) followed by a stream of nitrogen to transfer the [$^{18}$F]Flurpiridaz onto the second cartridge and trap the more lipophilic chemical and radiochemical impurities. The second SPE cartridge was then eluted with a 45% ethanolic solution (7 mL) to elute the [$^{18}$F]Flurpiridaz into the product vial. The 45 mL product vial was composed of water (42 mL), ethanol (3 mL) and ascorbic acid (50 mg/mL).

The non decay corrected yield was 40-44%, resulting in a product with an RAC of 1,700-2,000 MBq/mL. The RCP of the final product was 97-98%. Two radiolysis products were observed (1% and 1-2% respectively).

Example 5: Automated Synthesis and Purification of [$^{18}$F]Flurpiridaz

A FASTlab™ automated synthesizer (GE Healthcare Ltd) with cassette was used. The tC18 cartridge was obtained from Waters Limited (address as above). Precursor 1 was reacted with [$^{18}$F]fluoride on the FASTlab™ according to Example 3 to give [$^{18}$F]Flurpiridaz.

Purification.

Figure 4:
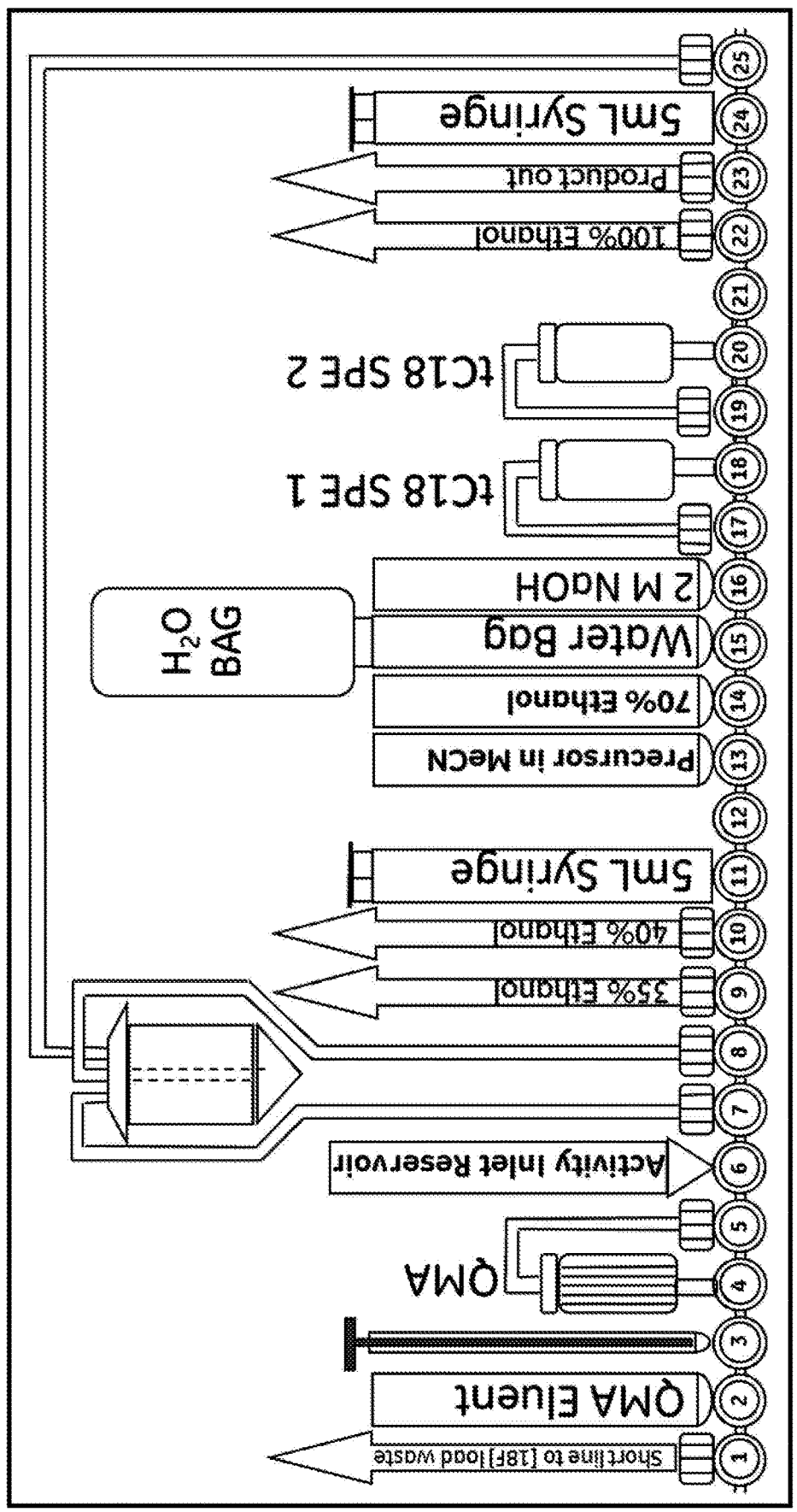
FIG. 4 shows the layout of a FASTlab™ cassette suitable for carrying out the method of the invention.

The cassette configuration is given in FIG. 4. Three external solvent vials are used on the cassette for the SPE purification in addition to the formulation vial:
Position 9=35% ethanol (or 40% acetonitrile) in water;
Position 10=40% ethanol (or 45% ethanol) in water;
Position 22=100% ethanol
Position 23=23 mL water for formulation.
Other cassette positions:
Position 14=70% ethanol in water (or blank)
Position 17: Tubing to the tC18 cartridge (SPE1) in Position 18;
Position 18: tC18 cartridge;
Position 19: Tubing to the tC18 cartridge (SPE2) in Position 18;
Position 20: tC18 cartridge;
FASTlab™ procedure.

In the following, P refers to the Position of the cassette. S2 and S3 refer to syringe 2 and syringe 3:

(i) the first part of the purification process was conditioning with full S2 fill with ethanol from P22, followed by a full S2 fill of water from P15.

(ii) the hydrolysed crude product was diluted with water to 7 mL total volume in S2 and then slowly trapped onto SPE1.

(iii) SPE1 was washed with 5×5 mL 35% ethanol (or 10-14 mL 40% acetonitrile) from position 9 via S2.

(iv) SPE1 and SPE2 were washed with 3×5 mL 40% ethanol (or 21-25 mL 40% acetonitrile) from position 10 via S2 to transfer [$^{18}$F]Flurpiridaz from SPE1 onto SPE2.

(v) the product was eluted from SPE2 with 70% ethanol (or 45% ethanol if acetonitrile method) solution from P14.

(vi) SPE2 was dried with a flow of nitrogen to ensure all of the product was transferred to the product collection vial (FIG. 4)

Example 6: Radiosynthesis of [$^{18}$F]Flurpiridaz with MeCN-Based SPE Purification

[$^{18}$F]-fluoride (ca. 100 GBq) is produced using a GE Medical Systems PETtrace cyclotron with a silver target via the [$^{18}$O](p,n)[$^{18}$F] nuclear reaction. Total target volumes of 3.2-4.8 mL are used. The radiofluoride is trapped on a Waters QMA cartridge (pre-conditioned with carbonate), and the fluoride is eluted with a solution of tetrabutylammonium hydrogen carbonate (22 mg) in water (100 µL) and acetonitrile (400 µL). Nitrogen is used to drive the solution off the QMA cartridge to the reaction vessel.

The [$^{18}$F]fluoride is dried for 9 minutes at 120° C. under a steady stream of nitrogen and vacuum. The precursor (10.2 mg) in MeCN (1.7 mL) is added to the dried [$^{18}$F]-fluoride and the reaction mixture is heated at 120° C. for 10 minutes. The crude product is diluted with water (5.3 mL) and loaded onto a tC18 SPE cartridge (Waters, product number WAT036800) and is purified using the method described below.

Sodium hydroxide (2 M, ca. 3 mL) is passed through the SPE cartridge at a slow flow rate to hydrolyse the crude product. The SPE cartridge is then washed with aqueous solution (14 mL) to wash away the acetonitrile, NaOH and hydrophilic chemical and radiochemical impurities. Then the SPE cartridge is washed with a 40% acetonitrile solution in water (10.5 mL) to remove the hydroxy impurity. In an alternative, the SPE cartridge could be washed with NaOH here either instead of or in addition to the earlier NaOH step. After this, the first SPE cartridge is connected in series to a second SPE cartridge (Waters, product number WAT036800) and the two are washed with further 40% acetonitrile water solution (24.5 mL) followed by a stream of nitrogen to transfer the [$^{18}$F]Flurpiridaz onto the second cartridge and trap the more lipophilic chemical and radiochemical impurities. The second SPE cartridge (optionally washed before ethanol elution) is then eluted with a 45% ethanolic solution (9 mL, 3-9 mL fraction collected in product vial) followed by water (4 mL) and a stream of nitrogen to elute the [$^{18}$F]Flurpiridaz into the product vial.

The invention claimed is:

1. A method for production of an $^{18}$F-labelled radiotracer compound comprising in an automated cassette system:
    reacting a precursor compound with $^{18}$F-fluoride in the presence of (2,2,6,6-Tetramethylpiperidin-1-yl)oxyl (TEMPO) and acetonitrile (MeCN) to obtain the $^{18}$F-labelled compound wherein:
    said precursor compound is of Formula I:

BTM-LINKER-LG (I)

wherein:
    BTM is an analogue of pyridaben;
    LINKER is an alkylene or an alkoxyalkylene; and,
    LG is a sulfonate-containing leaving group; and
    said $^{18}$F-labelled compound is of Formula II:

BTM-LINKER-$^{18}$F (II)

wherein BTM and LINKER are as defined for Formula I;
    purifying said $^{18}$F-labelled compound by means of a first solid phase extraction (SPE) cartridge in the automated cassette system, wherein said purification does not comprise high performance liquid chromatography (HPLC); and
    eluting the $^{18}$F-labelled radiotracer from a second SPE cartridge wherein the starting radioactivity is at least 100 GBq.

2. The method as defined in claim 1 wherein said precursor compound is a compound of Formula Ia:

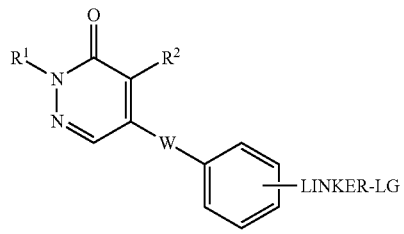

and said $^{18}$F-labelled compound is a compound of Formula IIa:

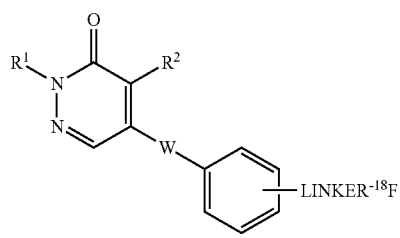

wherein:
R1 is an optionally substituted C1-6 alkyl;
R2 is hydrogen or halo;
W is an optionally substituted alkylene or heteroalkylene;
LINKER and LG are as defined in claim 1.

3. The method as defined in claim 2 wherein R$^1$ is C$_{1-6}$ alkyl.

4. The method as defined in claim 2 wherein R$^1$ is methyl, ethyl, propyl, n-butyl, s-butyl, or t-butyl.

5. The method as defined in claim 2 wherein R$^2$ is halo.

6. The method as defined in claim 2 wherein R$^2$ is chloro.

7. The method as defined in claim 2 wherein W is heteroalkylene.

8. The method as defined in claim 2 wherein W is alkoxyalkylene.

9. The method as defined in claim 1 wherein said compound of Formula I is a compound of Formula Ib:

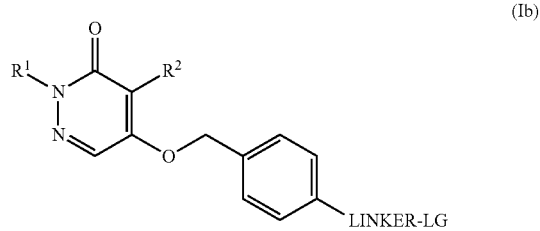

and said compound of Formula II is a compound of Formula IIb:

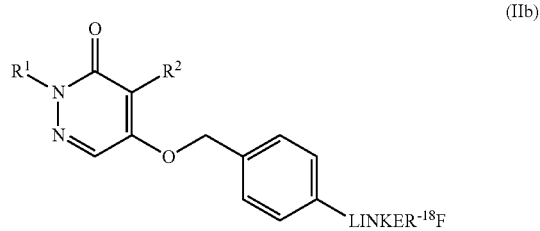

R$^1$ is an optionally substituted C$_{1-6}$ alkyl;
R$^2$ is hydrogen or halo;
LINKER is an alkylene or an alkoxyalkylene; and,
LG is a sulfonate-containing leaving group.

10. The method as defined in claim 1 wherein said compound of Formula I is:

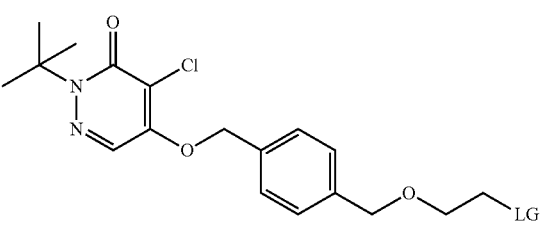

wherein LG is a sulfonate-containing leaving group;

and said compound of Formula II is:

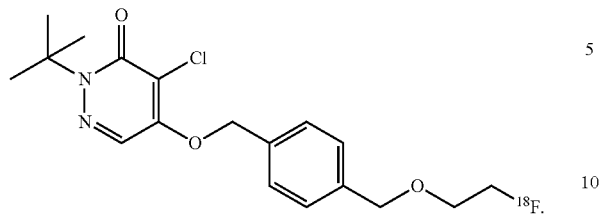

11. The method as defined in claim 1 wherein LG is selected from mesylate, tosylate, triflate, nosylate, or 1,2-cyclic sulfate.

12. The method as defined in claim 11 wherein LG is tosylate.

13. The method as defined in claim 1 wherein said precursor compound is dissolved in acetonitrile.

14. The method as defined in claim 1 wherein said TEMPO is present in a molar ratio to the precursor compound of between 0.01:1 and 5:1.

15. The method as defined in claim 1 wherein the starting radioactivity is between 100-1000 GBq.

16. The method as defined in claim 15 wherein the starting radioactivity is between 100-750 GBq.

* * * * *